United States Patent
Komiya et al.

(10) Patent No.: US 11,234,668 B2
(45) Date of Patent: Feb. 1, 2022

(54) IMAGING CONTROL APPARATUS AND RADIOGRAPHIC IMAGING SYSTEM

(71) Applicant: Konica Minolta, Inc., Tokyo (JP)

(72) Inventors: Satoshi Komiya, Hino (JP); Koutarou Kanamori, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 15 days.

(21) Appl. No.: 16/921,122

(22) Filed: Jul. 6, 2020

(65) Prior Publication Data
US 2021/0000439 A1    Jan. 7, 2021

(30) Foreign Application Priority Data
Jul. 3, 2019 (JP) .............................. JP2019-124140

(51) Int. Cl.
*A61B 6/00* (2006.01)

(52) U.S. Cl.
CPC .............. *A61B 6/54* (2013.01); *A61B 6/4405* (2013.01); *A61B 6/4452* (2013.01); *A61B 6/467* (2013.01); *A61B 6/482* (2013.01); *A61B 6/563* (2013.01)

(58) Field of Classification Search
CPC .. H05G 1/44; A61B 6/542; A61B 6/56; A61B 6/54; A61B 6/4405; A61B 90/50; A61B 6/467; G01T 1/185
See application file for complete search history.

(56) References Cited

U.S. PATENT DOCUMENTS

2019/0076107 A1* 3/2019 Uehara .................... A61B 6/46

FOREIGN PATENT DOCUMENTS

JP        2018093954 A    6/2018

* cited by examiner

*Primary Examiner* — Don K Wong
(74) *Attorney, Agent, or Firm* — Cantor Colburn LLP

(57) ABSTRACT

An imaging control apparatus includes a hardware processor. The hardware processor is capable of sending, to a console, a command indicating permission of radiation emission. The console controls a radiation emitting apparatus that emits radiation. The hardware processor is also capable of outputting a first control signal to a radiographic imaging apparatus that generates a radiograph based on the first control signal.

4 Claims, 4 Drawing Sheets

IMAGING CONTROL APPARATUS AND RADIOGRAPHIC IMAGING SYSTEM

CROSS-REFERENCE TO RELATED APPLICATIONS

The present invention claims priority under 35 U.S.C. § 119 to Japanese Application No. 2019-124140 filed Jul. 3, 2019, the entire content of which is incorporated herein by reference.

BACKGROUND

Technological Field

The present disclosure relates to an imaging control apparatus and a radiographic imaging system.

Description of the Related Art

In order to configure a radiographic imaging system by using a radiation emitting apparatus that emits radiation and a radiographic imaging apparatus that generates a radiograph(s) corresponding to the received radiation, it is necessary to create a state in which the radiation emitting apparatus and the radiographic imaging apparatus can operate in cooperation with one another.

However, there are cases where a radiation emitting apparatus and a radiographic imaging apparatus cannot be linked (i.e. cannot be made to cooperate) with one another because they employ different linkage systems due to, for example, different manufacturers. For example, there is a case where a radiation emitting apparatus is the one that is linked with peripherals (e.g. console) by software (by sending and receiving commands), whereas a radiographic imaging apparatus is the one that is linked with peripherals by hardware (by ON/OFF of signals through cables).

In order to solve such a problem, in recent years, there has been proposed a technique for linking a radiation emitting apparatus and a radiographic imaging apparatus employing different linkage systems with one another.

For example, there is disclosed in JP 2018-093954 A a technique of connecting a control unit that sends an emission synchronizing signal to a radiation emitting apparatus and sending a readout synchronizing signal to a radiographic imaging apparatus to the radiation emitting apparatus and the radiographic imaging apparatus, and causing the radiation emitting apparatus and the radiographic imaging apparatus to operate on the basis of the respective synchronizing signals.

SUMMARY

However, such a conventional control unit as disclosed in JP2018-093954A is the one that is connected to a radiation emitting apparatus and a radiographic imaging apparatus through a hardware interface of the radiation emitting apparatus or a peripheral connected to (linked with) the radiation emitting apparatus.

Hence, when neither a radiation emitting apparatus nor its peripheral is provided with a hardware interface, in order to link the radiation emitting apparatus and a radiographic imaging apparatus employing different linkage systems with one another by using the conventional control unit, it is necessary to take some measure, such as modifying at least one of the radiation emitting apparatus, the peripheral and the radiographic imaging apparatus.

The present disclosure has been conceived in view of the above problems, and objects of the present disclosure include providing an imaging control apparatus for linking a radiation emitting apparatus and a radiographic imaging apparatus employing different linkage systems with one another, the imaging control apparatus capable of linking a radiation emitting apparatus and a radiographic imaging apparatus with one another even when neither the radiation emitting apparatus nor a peripheral connected to the radiation emitting apparatus is provided with a hardware interface.

In order to achieve at least one of the abovementioned objects, according to a first aspect of the present disclosure, there is provided an imaging control apparatus including a hardware processor that:

is capable of sending, to a console that controls a radiation emitting apparatus that emits radiation, a command indicating permission of radiation emission; and is capable of outputting a first control signal to a radiographic imaging apparatus that generates a radiograph based on the first control signal.

According to a second aspect of the present disclosure, there is provided a radiographic imaging system including:

a radiation emitting apparatus that is configured to be movable, and emits radiation;

a console that controls radiation emission of the radiation emitting apparatus in response to receiving a command indicating permission of radiation emission;

a hardware processor that sends the command to the console; and a portable radiographic imaging apparatus that generates a radiograph based on a first control signal, wherein the hardware processor outputs the first control signal to the portable radiographic imaging apparatus.

According to a third aspect of the present disclosure, there is provided a radiographic imaging system including:

a radiation emitting apparatus that is capable of emitting first radiation having relatively low energy and second radiation having relatively high energy in order;

a console that controls radiation emission of the radiation emitting apparatus in response to receiving a command indicating permission of radiation emission; and a hardware processor that sends the command to the console; and a radiographic imaging apparatus that is capable of generating a first radiograph corresponding to the first radiation and a second radiograph corresponding to the second radiation in order based on a first control signal, wherein the hardware processor outputs the first control signal to the radiographic imaging apparatus, and wherein the console generates a difference image between the first radiograph and the second radiograph in response to the first radiograph and the second radiograph being generated.

BRIEF DESCRIPTION OF THE DRAWINGS

The objects, advantages, and characteristics arranged by one or more embodiments of the present invention will become more fully understood from the detailed description given hereinbelow and the appended drawings that are given by way of illustration only, and thus are not intended as a definition of the limits of the present invention, wherein.

DETAILED DESCRIPTION OF EMBODIMENTS

Hereinafter, one or more embodiments of the present invention are described in detail with reference to the drawings. However, the scope of the present invention is not limited to the embodiments or illustrated examples.

1. Radiographic Imaging System

Figure 1:
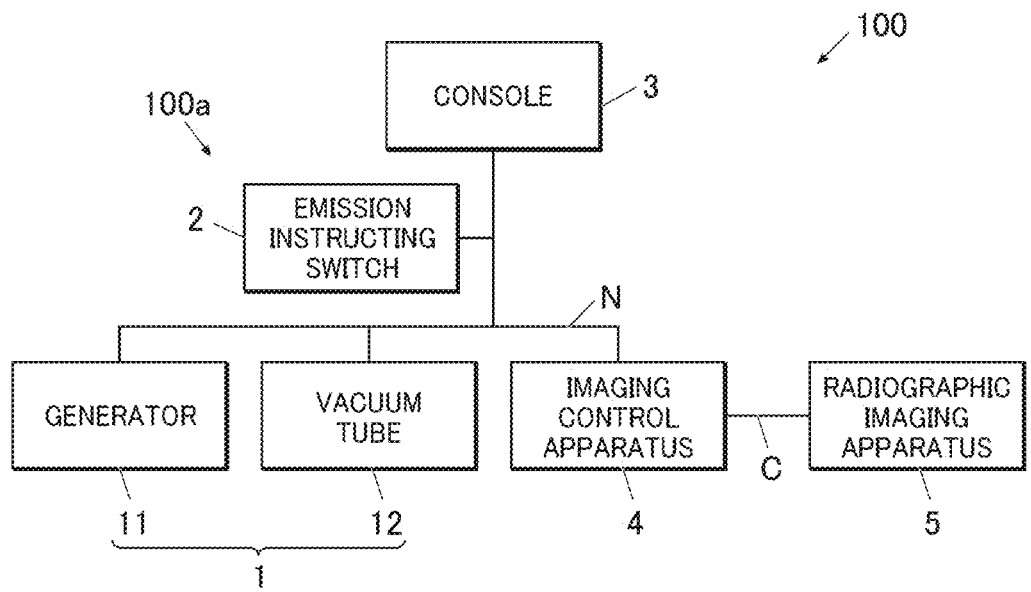
FIG. 1 is a block diagram showing a radiographic imaging system according to an embodiment(s) of the present disclosure.

First, a schematic configuration of a radiographic imaging system (hereinafter "system 100") according to an embodiment(s) will be described. FIG. 1 is a block diagram showing the system 100.

As shown in FIG. 1, the system 100 includes a radiation emitting apparatus (hereinafter "emitting apparatus 1"), an emission instructing switch 2, a console 3, an imaging control apparatus 4 and a radiographic imaging apparatus (hereinafter "imaging apparatus 5").

The emitting apparatus 1, the console 3 and the emission instructing switch 2 constitute a radiation emitting system 100a.

The apparatuses (emitting apparatus 1, emission instructing switch 2, console 3) constituting the radiation emitting system 100a and the imaging control apparatus 4 are linked (i.e. made to cooperate) with one another by software. More specifically, these apparatuses are connected to one another through a communication network N (e.g. Ethernet®) and linked with one another by sending and receiving various commands to and from one another.

The imaging control apparatus 4 and the imaging apparatus 5 are linked (i.e. made to cooperate) with one another by hardware. More specifically, these apparatuses are connected to one another through a signal cable C and linked with one another by ON/OFF of various output or input signals.

The system 100 may be connectable to other systems, such as a radiology information system (RIS), a picture archiving and communication system (PACS) (both not shown).

The system 100 may include an imaging stand (not shown) that holds the imaging apparatus 5.

The system 100 may be fixed in an imaging room or may be configured as a nursing cart (the emitting apparatus 1 configured to be movable and the imaging apparatus 5 being portable).

(1-1. Radiation Emitting Apparatus)

The emitting apparatus 1 includes a generator 11 and a vacuum tube 12 (e.g. X-ray tube).

By taking, as a trigger, a timing of receiving emission control of the console 3, the generator 11 applies, to the vacuum tube 12, a voltage suitable for preset imaging conditions (e.g. imaging mode (still image shooting, moving image shooting or another type of imaging/shooting), condition of a subject (site (part) to be imaged, body build, imaging direction, etc.), and condition of radiation emission (tube voltage, tube current, emission time, current-time product (mAs value), etc., and frame rate when the imaging mode is moving image shooting)).

As the "emission control", which the console 3 performs on the emitting apparatus 1, the console 3 may send an emission command or perform ON/OFF switching of an emission timing signal output to the emitting apparatus 1, for example.

When the voltage is applied from the generator 11, the vacuum tube 12 emits a dose of radiation (e.g. X-rays) corresponding to the applied voltage.

By taking, as a trigger, the timing of receiving emission control of the console 3, the emitting apparatus 1 thus configured emits radiation in a form suitable for the set imaging conditions.

For example, when the set imaging mode is still image shooting, the emitting apparatus 1 emits a predetermined dose of radiation only once for a predetermined emission time.

On the other hand, when the set imaging mode is moving image shooting, the emitting apparatus 1 emits a predetermined dose of pulsed radiation a predetermined number of times at predetermined intervals (on a predetermined cycle), wherein each emission time is shorter than the emission time for still image shooting.

In the case of moving image shooting, the emitting apparatus 1 may keep emitting radiation while the emission instructing switch 2 is being operated.

(1-2. Emission Instructing Switch)

The emission instructing switch 2 outputs a first stage signal and a second stage signal to the console 3, and performs ON/OFF switching of the first stage signal and the second stage signal depending on how the switch 2 is operated.

The emission instructing switch 2 of this embodiment is a two-stage operable push-button having a first stage and a second stage. When the first stage is pressed, the emission instructing switch 2 turns on the first stage signal to be output to the console 3, and when the second stage is pressed, the emission instructing switch 2 turns on the second stage signal to be output to the console 3.

Although FIG. 1 shows a case where the emission instructing switch 2 is connected to the communication network N, the emission instructing switch 2 may be connected to the generator 11 or the console 3.

(1-3. Console)

The console 3 is composed of a PC, a portable terminal or a dedicated apparatus.

The console 3 according to this embodiment can set the abovementioned imaging conditions in the emitting apparatus 1.

Further, the console 3 controls radiation emission of the emitting apparatus 1 in response to receiving, from the imaging control apparatus 4, a command indicating permission of radiation emission (hereinafter "emission permission command").

More specifically, when the console 3 receives the emission permission command, and the second stage signal input from the emission instructing switch 2 is ON, the console 3 performs emission control on the emitting apparatus 1 suitable for the set imaging conditions.

The console 3 may include a display (not shown) and display the set imaging conditions on the display.

The console 3 may obtain radiographs generated by the imaging apparatus 5 and display the radiographs on the display.

The console 3 may display, on the display, whether or not the emission permission command has been received (whether or not the imaging apparatus 5 is ready to be irradiated).

(1-4. Imaging Control Apparatus)

The imaging control apparatus 4 is composed of a PC or a dedicated apparatus.

The imaging control apparatus 4 outputs a readout timing signal (first control signal) to the imaging apparatus 5.

The imaging control apparatus 4 sends the emission permission command to the console 3.

The imaging control apparatus 4 will be detailed later.

(1-5. Radiographic Imaging Apparatus)

The imaging apparatus 5 includes a radiation detector, a scanning drive unit, a reader and a signal input unit (all not shown).

The radiation detector is configured such that pixels each having a radiation detection element and a switch element are arranged two-dimensionally (in a matrix). Each radiation detection element generates electric charge(s) corresponding to a dose of received radiation.

The scanning drive unit controls ON/OFF of each switch element.

The reader reads out the amount of charges discharged from each pixel as a signal value, and generates data of a radiograph from a plurality of signal values.

The signal input unit includes a connector for receiving the readout timing signal (for connecting the signal cable C for the readout timing signal).

The imaging apparatus 5 thus configured starts preparing for imaging by taking, as a trigger, a timing at which a power source is turned on, at which the imaging apparatus 5 is connected to the imaging control apparatus 4, or at which the imaging apparatus 5 receives a predetermined control signal from the imaging control apparatus 4, for example. Examples of the preparation for imaging include warming up the reader and generating a dark image for offset correction.

When completing the preparation for imaging, the imaging apparatus 5 turns on a preparation completion signal output to the imaging control apparatus 4.

The imaging apparatus 5 that has completed the preparation for imaging can generate a radiograph (frame) by taking, as a trigger, a timing at which the readout timing signal input from the imaging control apparatus 4 is turned on.

For generating a radiograph, the imaging apparatus 5 receives radiation from the vacuum tube 12 through a subject (person, animal or object). Consequently, the imaging apparatus 5 generates a radiograph of the subject corresponding to the received radiation.

The imaging apparatus 5 may have a built-in scintillator, and convert received radiation into light having another wavelength, such as visible light, with the scintillator, and generate electric charges corresponding to the light obtained by the conversion, which is called indirect type, or may generate electric charges directly from received radiation without a scintillator or the like, which is called direct type.

In the case of moving image shooting, instead of generating a frame each time the input readout timing signal is turned on, the imaging apparatus 5 may automatically generate a radiograph a predetermined number of times at predetermined intervals (on a predetermined cycle), thereby generating a plurality of radiographs, in response to receiving, one time, a signal serving as a trigger for starting imaging.

The imaging apparatus 5 may include a communication unit for sending generated data of radiographs to other apparatuses.

2. Details of Imaging Control Apparatus

Figure 2:
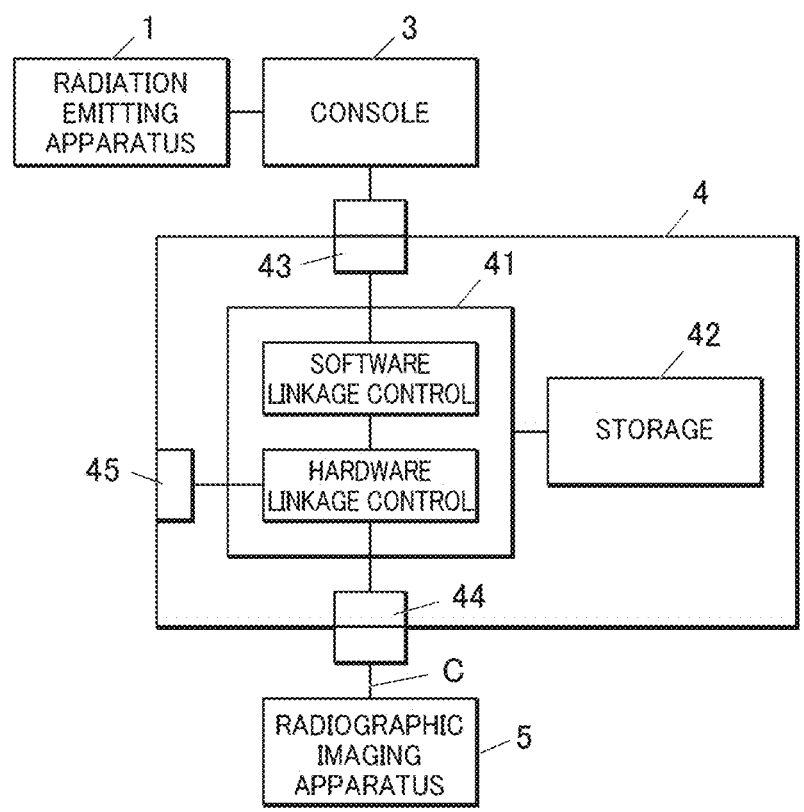
FIG. 2 is a block diagram showing an imaging control apparatus included in the radiographic imaging system shown in FIG. 1.

Next, the imaging control apparatus 4 included in the system 100 will be detailed. FIG. 2 is a block diagram showing the imaging control apparatus 4.

(2-1. Configuration)

As shown in FIG. 2, the imaging control apparatus 4 includes a controller 41 (hardware processor), a storage 42, a first connection part 43 and a second connection part 44.

The controller 41 includes a central processing unit (CPU) and a random access memory (RAM).

The CPU of the controller 41 reads out various programs stored in the storage 42, loads the programs into the RAM, and performs various processes in accordance with the loaded programs, thereby performing centralized control of operation of the components of the imaging control apparatus 4.

The storage 42 is composed of a nonvolatile semiconductor memory, a hard disk and/or the like.

The storage 42 stores, for example, various programs that are executed by the controller 41.

The first connection part 43 includes a connector for connecting, to the controller 41, an information cable that can transmit various commands including the emission permission command.

The second connection part 44 includes a connector for connecting, to the controller 41, the signal cable C that can transmit various signals including the readout timing signal.

(2-2. Operation)

The controller 41 of the imaging control apparatus 4 thus configured can set the imaging conditions in the imaging apparatus 5.

The setting may be performed manually on the basis of a user operation(s) on an operation unit (not shown) included in the imaging control apparatus 4, or may be performed automatically in accordance with the setting state of the imaging conditions received from the console 3.

The controller 41 may have a function of checking whether or not the imaging conditions set in the imaging apparatus 5 are the same as the imaging conditions set in the emitting apparatus 1 by the console 3.

The controller 41 sends the emission permission command to the console 3 through the first connection part 43.

The controller 41 according to this embodiment sends the emission permission command by taking, as a trigger, a timing at which the preparation completion signal input from the imaging apparatus 5 is turned on.

The controller 41 outputs the readout timing signal to the imaging apparatus 5 through the second connection part 44 by taking, as a trigger, a timing at which a power source is turned on, at which the imaging control apparatus 4 is connected to the imaging apparatus 5, or at which the imaging control apparatus 4 receives a predetermined control signal from the console 3 or the imaging apparatus 5, for example.

The controller 41 performs ON/OFF switching of the readout timing signal in a form suitable for the set imaging conditions.

When the set imaging mode is still image shooting, the controller 41 performs, only one time per sending of the emission permission command, a process of turning on the readout timing signal and, after a predetermined time has elapsed, turning off the readout timing signal.

On the other hand, when the set imaging mode is moving image shooting, the controller 41 repeats, multiple times at predetermined intervals (on a predetermined cycle) per sending of the emission permission command, the process of turning on the readout timing signal and, after a predetermined time has elapsed, turning off the readout timing signal.

The imaging control apparatus 4 may include a third connection part 45 including a connector for connecting a signal cable that can transmit various commands, so that the controller 41 can output the emission timing signal (second control signal) to other apparatuses through the third connection part 45.

Consequently, when a radiation emitting apparatus as a connecting destination has a connector for connecting a signal cable and is configured to be capable of emitting radiation by taking, as a trigger, a timing at which the emission timing signal input through the connector is turned on, a radiation emitting system and the imaging apparatus 5 can be linked with one another by a conventional connecting method.

That is, use of the imaging control apparatus 4 according to this embodiment makes it possible to link the imaging apparatus 5 and a radiation emitting system as a connecting destination with one another, regardless of whether or not the radiation emitting system has a connector for connecting a signal cable.

3. Procedure of Imaging

Figure 3:
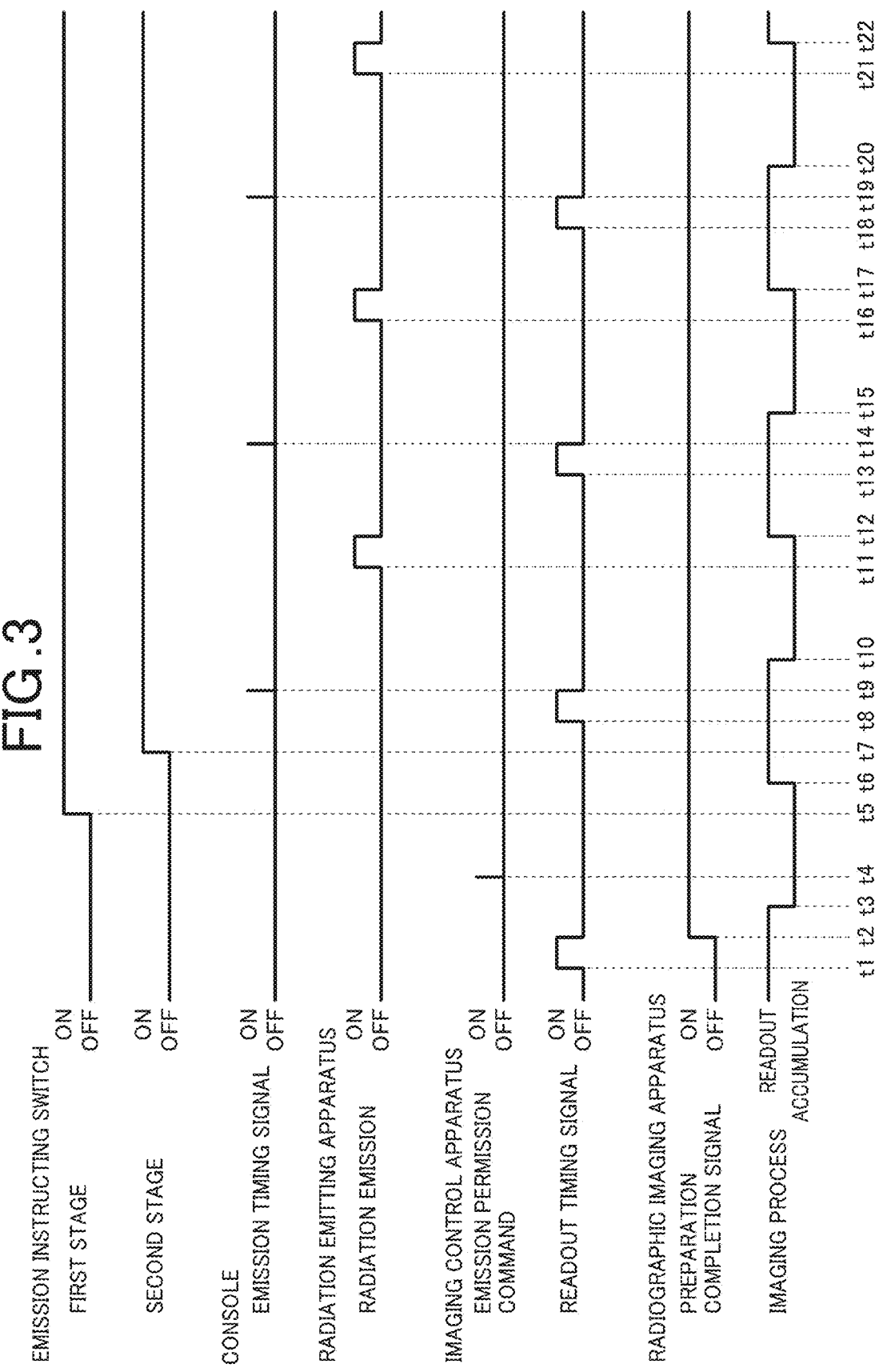
FIG. 3 is a timing chart showing an example of operation of the radiographic imaging system according to the embodiment.

Next, a procedure of imaging using the above-described system 100 will be described in the case of moving image shooting as an example. FIG. 3 is a timing chart showing an example of the operation of the system 100.

First, a subject is placed between the vacuum tube 12 and the imaging apparatus 5 that are disposed so as to face one another with a space in between. Then, a photographer inputs imaging conditions into the console 3 or the imaging control apparatus 4.

Then, the imaging control apparatus 4 repeats, at predetermined intervals (on a predetermined cycle), ON/OFF of the readout timing signal input to the imaging apparatus 5 (ON at t1, t8, t13, t18, . . . ).

When the repetition of ON/OFF of the readout timing signal input from the imaging control apparatus 4 starts, the imaging apparatus 5 starts preparing for imaging.

When completing the preparation for imaging, the imaging apparatus 5 turns on the preparation completion signal output to the imaging control apparatus 4 (t2), and repeats a process of accumulating charges (t3 to t6, t10 to t12, t15 to t17, t20 to t22, . . . ) and reading out the charges ( . . . to t3, t6 to t10, t12 to t15, t17 to t20, t22 to . . . ) at predetermined intervals (on a predetermined cycle), namely performs the process each time the readout timing signal input from the imaging control apparatus 4 is turned on.

When the imaging control apparatus 4 detects that the preparation completion signal input from the imaging apparatus 5 is ON, the imaging control apparatus 4 sends the emission permission command to the console 3 (t4). This puts the emitting apparatus 1 in a state in which the emitting apparatus 1 can emit radiation.

When the photographer presses the first stage of the emission instructing switch 2, the emission instructing switch 2 turns on the first stage signal to be output to the emitting apparatus 1 (t5).

When the emitting apparatus 1 detects that the first stage signal is ON, the emitting apparatus 1 starts preparing to emit radiation (e.g. rotating a rotatable anode of the vacuum tube 12).

When the photographer presses the second stage of the emission instructing switch 2, the emission instructing switch 2 turns on the second stage signal to be output to the emitting apparatus 1 (t7).

When the console 3 detects that the second stage signal is ON with the emission permission command received, the console 3 performs emission control on the emitting apparatus 1.

When the generator 11 of the emitting apparatus 1 receives emission control of the console 3, the generator 11 repeatedly applies, to the vacuum tube 12, a voltage suitable for the imaging conditions.

Each time the voltage is applied from the generator 11, the vacuum tube 12 emits radiation corresponding to the voltage (t11, t16, t21, . . . ).

The radiation emitted (produced) by the vacuum tube 12 is emitted (applied) to the subject and the imaging apparatus 5 behind the subject. Part of the radiation passes through the subject and enters the imaging apparatus 5.

While the emitting apparatus 1 repeatedly emits radiation, the imaging apparatus 5 repeats the process of accumulating charges (t3 to t6, t10 to t12, t15 to t17, t20 to t22, . . . ) and reading out the charges ( . . . to t3, t6 to t10, t12 to t15, t17 to t20, t22 to . . . ) at predetermined intervals (on a predetermined cycle), namely performs the process each time the readout timing signal input from the imaging control apparatus 4 is turned on.

A length of time in which the imaging apparatus 5 turns off the switch elements, thereby accumulating charges in the respective pixels, is sufficiently longer than a length of time of one radiation emission. Hence, as long as the interval(s) at which radiation is emitted (radiation emission cycle) that is set in the emitting apparatus 1 is equal to the interval(s) at which a frame is generated (frame generation cycle) that is set in the imaging apparatus 5, radiation enters the imaging apparatus 5 while the imaging apparatus 5 is in the accumulation state.

Thus, a moving image of the subject composed of a plurality of frame images is obtained.

4. Advantageous Effects

The imaging control apparatus 4 described above can be linked with the console 3 by software by sending the emission permission command to the console 3, and can be linked with the imaging apparatus 5 by hardware by outputting the control signal (first control signal) to the imaging apparatus 5.

Hence, use of the imaging control apparatus 4 makes it possible to link the emitting apparatus 1 and the imaging apparatus 5, which use different linkage systems, with one another even when neither the emitting apparatus 1 nor a peripheral (console 3) connected to the emitting apparatus 1 is provided with a hardware interface.

5. Modifications

Needless to say, the present invention is not limited to the above embodiment(s), and can be appropriately modified without departing from the scope of the present invention.
(5-1. Energy Subtraction Imaging Function)

For example, the system 100 may have a function of energy subtraction imaging (generating radiographs with obstacles (e.g. bones) removed).

In this case, the emitting apparatus 1, the imaging apparatus 5 and the console 3 are configured as follows.

Figure 4:
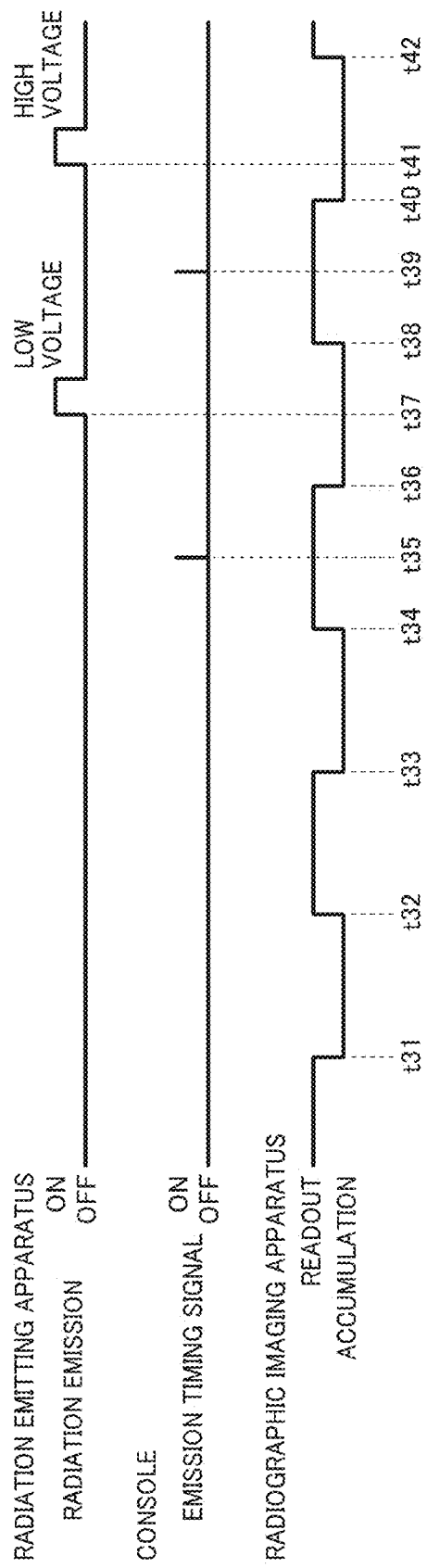
FIG. 4 is a timing chart showing the example of operation of the radiographic imaging system according to a modification of the embodiment.

For example, as shown in FIG. 4, the emitting apparatus 1 is configured to be capable of emitting first radiation having relatively low energy (voltage applied by the generator 11 to the vacuum tube 12) and second radiation having relatively high energy in order (t37, t41) per imaging operation (press of the emission instructing switch 2).

The imaging apparatus 5 is configured to be capable of generating a first radiograph corresponding to the first radiation and a second radiograph corresponding to the second radiation in order on the basis of the readout timing signal.

More specifically, the imaging apparatus 5 generates the first radiograph by reading signal values (t38 to t40) based on charges accumulated by emission of the first radiation (t37), and generates the second radiograph by reading signal values (t42 to . . . ) based on charges accumulated by emission of the second radiation (t41).

The console 3 is configured to have an image difference function in addition to the function of controlling radiation emission of the emitting apparatus 1.

More specifically, the console 3 is configured to be capable of generating a difference image between the first radiograph and the second radiograph.

Not the console 3 but another apparatus (e.g. imaging apparatus 5) may be configured to have the function of generating difference images.

(5-2. Long-Length Imaging Function)

The system 100 may have a function of long-length imaging (generating a long image composed of radiographs joined together).

Figure 5:
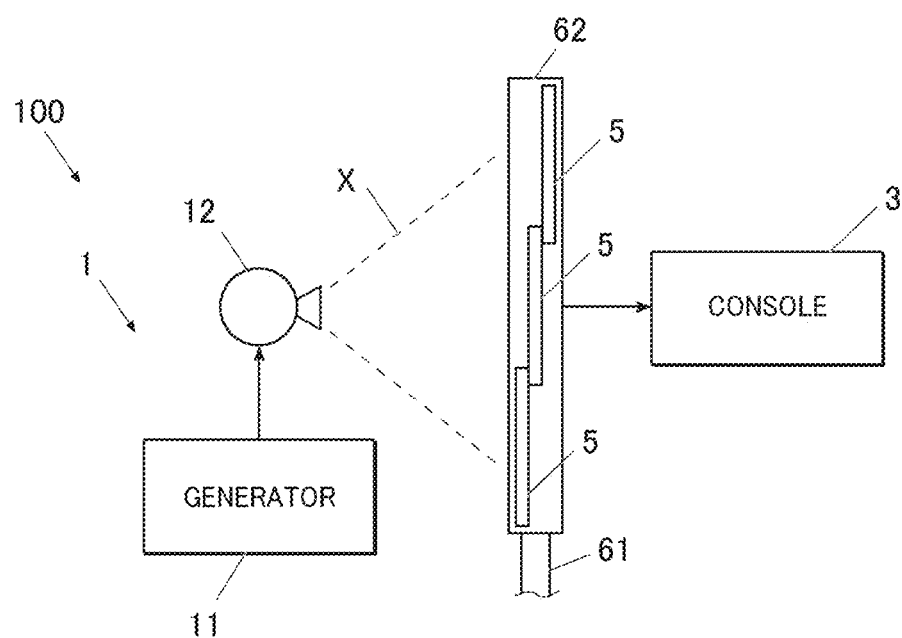
FIG. 5 is a schematic view showing the radiographic imaging system according to a modification of the embodiment.

In this case, the system 100 is configured as shown in FIG. 5, for example.

More specifically, the system 100 includes a plurality of imaging apparatuses 5 and an imaging stand (wall stand) 6 where the plurality of imaging apparatuses 5 can be mounted.

The imaging stand 6 includes a support 61 and a holder 62.

The holder 62 is supported by the support 61 and formed to be a cuboid, for example. In the holder 62, mounting parts as rooms where the imaging apparatuses 5 are mounted are formed so as to line up along the longer direction of the holder 62.

The console 3 is configured to have an image combining function in addition to the function of controlling radiation emission of the emitting apparatus 1.

More specifically, the console 3 is configured to be capable of generating one long image by combining radiographs generated by the respective imaging apparatuses 5.

The system 100 thus configured can generate a long image of the subject by performing imaging one time in a state in which the longer direction of the subject (body axis or legs of the subject) is parallel to the longer direction of the holder 62.

Instead of generating a plurality of radiographs simultaneously by using a plurality of imaging apparatuses 5, the system 100 may have one imaging apparatus 5 and an imaging stand that can move the imaging apparatus 5 mounted thereon.

In this case, the imaging stand includes the support 61, a holder and a moving mechanism.

The holder is formed to be rectangular, for example. In the holder, one mounting part is formed.

The moving mechanism is configured to be movable in the vertical direction with respect to the support 61 under the control of the console 3, and supports the holder.

The system 100 thus configured can generate a long image of the subject as with the above case by alternating moving the imaging apparatus 5 with performing imaging with the imaging apparatus 5 multiple times in a state in which the longer direction of the subject is parallel to the moving direction of the imaging apparatus 5.

Although some embodiments or the like of the present invention have been described and illustrated in detail, the disclosed embodiments or the like are made for purposes of not limitation but illustration and example only. The scope of the present invention should be interpreted by terms of the appended claims.

What is claimed is:

1. An imaging control apparatus comprising a hardware processor that:
   is capable of sending, to a console that controls a radiation emitting apparatus that emits radiation, a command indicating permission of radiation emission; and
   is capable of outputting a first control signal to a radiographic imaging apparatus that generates a radiograph based on the first control signal.

2. The imaging control apparatus according to claim 1, wherein the hardware processor is capable of outputting a second control signal to the radiation emitting apparatus that emits the radiation based on the second control signal.

3. A radiographic imaging system comprising:
   a radiation emitting apparatus that is configured to be movable, and emits radiation;
   a console that controls radiation emission of the radiation emitting apparatus in response to receiving a command indicating permission of radiation emission;
   a hardware processor that sends the command to the console; and
   a portable radiographic imaging apparatus that generates a radiograph based on a first control signal,
   wherein the hardware processor outputs the first control signal to the portable radiographic imaging apparatus.

4. A radiographic imaging system comprising:
   a radiation emitting apparatus that is capable of emitting first radiation having relatively low energy and second radiation having relatively high energy in order;
   a console that controls radiation emission of the radiation emitting apparatus in response to receiving a command indicating permission of radiation emission; and
   a hardware processor that sends the command to the console; and
   a radiographic imaging apparatus that is capable of generating a first radiograph corresponding to the first radiation and a second radiograph corresponding to the second radiation in order based on a first control signal,
   wherein the hardware processor outputs the first control signal to the radiographic imaging apparatus, and
   wherein the console generates a difference image between the first radiograph and the second radiograph in response to the first radiograph and the second radiograph being generated.

* * * * *